(12) United States Patent
Constantinis

(10) Patent No.: US 10,011,145 B2
(45) Date of Patent: Jul. 3, 2018

(54) APPARATUS AND METHOD FOR INSPECTING FLOODED CAVITIES IN A FLOATING OFFSHORE INSTALLATION

(71) Applicant: EM&I (MARITIME) LIMITED, St. Helier, Jersey, Channel Islands (JE)

(72) Inventor: Danny Constantinis, Wilmslow (GB)

(73) Assignee: EM&I (MARTIME) LIMITED, St. Helier, Channel Islands (JE)

( * ) Notice: Subject to any disclaimer, the term of this patent is extended or adjusted under 35 U.S.C. 154(b) by 240 days.

(21) Appl. No.: 15/039,487

(22) PCT Filed: Nov. 27, 2014

(86) PCT No.: PCT/GB2014/000489
§ 371 (c)(1),
(2) Date: May 26, 2016

(87) PCT Pub. No.: WO2015/079199
PCT Pub. Date: Jun. 4, 2015

(65) Prior Publication Data
US 2017/0021665 A1    Jan. 26, 2017

(30) Foreign Application Priority Data
Nov. 27, 2013  (GB) .................................. 1320927.5

(51) Int. Cl.
*B60B 9/00* (2006.01)
*F16L 41/04* (2006.01)
(Continued)

(52) U.S. Cl.
CPC .................. *B60B 9/00* (2013.01); *B63B 9/00* (2013.01); *F16L 41/04* (2013.01); *F16L 41/16* (2013.01);
(Continued)

(58) Field of Classification Search
CPC .. B60B 9/00; F16L 41/04; F16L 41/16; B63B 9/00; G01N 21/954
See application file for complete search history.

(56) References Cited

U.S. PATENT DOCUMENTS 3,776,574 A    12/1973  Henderson et al.
4,558,744 A *  12/1985  Gibb ..................... E21B 33/037
                                                        166/222
(Continued)

FOREIGN PATENT DOCUMENTS

GB    1 467 894    3/1977
GB    2 247 505    3/1992
(Continued)

OTHER PUBLICATIONS

International Search Report for International application No. PCT/GB2014/000489, Completed Feb. 5, 2015, dated Feb. 13, 2015, Authorized Officer Blazquez Lainez, ISA/EPO, 5 pgs.
(Continued)

*Primary Examiner* — John Fitzgerald
(74) *Attorney, Agent, or Firm* — Fay Sharpe LLP

(57) ABSTRACT

A threaded connection body is welded to the wall of a pipe, seachest or other flooded cavity within the hull of a ship or floating offshore installation. A sealed cutting apparatus is mounted via a valve unit n the connection body and a cutter extended through the open valve to form an opening in the wall. After retracting the cutter and closing the valve, the cutting apparatus is replaced by an inspection unit having a camera which is extended through the valve and the opening to inspect the cavity. After retracting the camera and closing the valve, the inspection unit is replaced by a plug deployment unit which advances a plug through the valve and screws it into the connection body. The valve unit can then
(Continued)

be removed and replaced with a cap so that the plug and the cap provide a double seal to the connection body.

16 Claims, 16 Drawing Sheets

(51) Int. Cl.
    *F16L 41/16*     (2006.01)
    *G01N 21/954*     (2006.01)
    *B63B 9/00*     (2006.01)
    *B63B 13/00*     (2006.01)
    *B63B 43/00*     (2006.01)

(52) U.S. Cl.
    CPC ...... *G01N 21/954* (2013.01); *B63B 2013/005* (2013.01); *B63B 2043/006* (2013.01); *G01N 2201/02* (2013.01)

(56) References Cited

U.S. PATENT DOCUMENTS

| | | | |
|---|---|---|---|
| 5,025,670 | A | 6/1991 | McNulty et al. |
| 5,513,930 | A | 5/1996 | Eathorne |
| 6,317,387 | B1 | 11/2001 | D'Amaddio et al. |
| 7,441,993 | B2 * | 10/2008 | Evans ............ F16L 41/06 137/318 |
| 2003/0106480 | A1 | 6/2003 | Harrie et al. |
| 2009/0007833 | A1 | 1/2009 | Olenio |
| 2009/0147270 | A1 | 6/2009 | Lehmann |

FOREIGN PATENT DOCUMENTS

| | | |
|---|---|---|
| JP | 52-118789 | 10/1977 |
| JP | 55-19631 | 2/1980 |
| JP | 61-132487 | 6/1986 |
| JP | 53-31797 | 12/1993 |
| JP | 50-155795 | 2/1998 |
| JP | 11-301570 | 11/1999 |
| JP | 04891685 B2 | 3/2012 |
| JP | 2013 047039 | 3/2013 |
| KR | 10-0540079 | 1/2006 |
| KR | 20-100092278 A | 8/2010 |
| KR | 20-2011-0012049 | 12/2011 |
| KR | 10-2012-0016471 | 2/2012 |
| NL | 7401259 | 8/1975 |
| NO | 311561 | 8/2000 |
| WO | WO 2010/022993 A2 | 3/2010 |
| WO | WO 2012/171091 A1 | 12/2012 |

OTHER PUBLICATIONS

Written Opinion of the International Searching Authority for International application No. PCT/GB2014/000489, dated Feb. 13, 2015, 6 pgs.

British Search Report dated May 21, 2014 for Application No. GB1320927.5.

"Hot Tapping"; Feb. 29, 2012; retrieved from the Internet at URL: https://web.archive.org/web/20120229062340/http://www.koppl.com/pdfs/Hottap.pdf; [retrieved on Feb. 5, 2015], pp. 2,3,4.

"Hot Tapping and Plugging Transmission Lines"; May 3, 2013; retrieved from the Internet at URL: https://www.youtube.com/watch?v=DJolmbxSMFE; [retrieved on Feb. 5, 2015].

"Pigging Wye Animation.wmv"; Dec. 9, 2010; retrieved from the Internet at URL: https://www.youtube.com/watch?v=VBPnBNcH5zo; [retrieved on Feb. 5, 2015].

\* cited by examiner

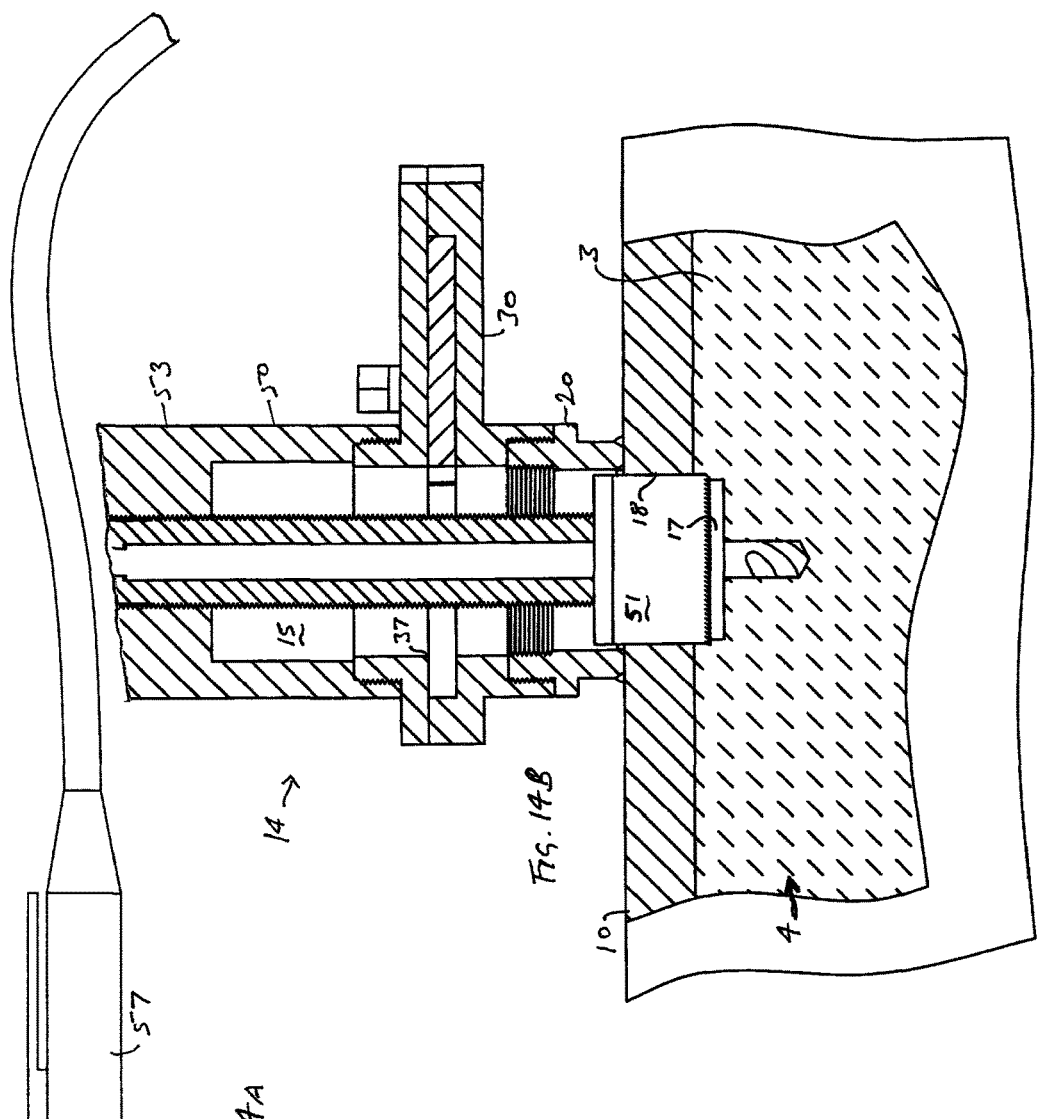
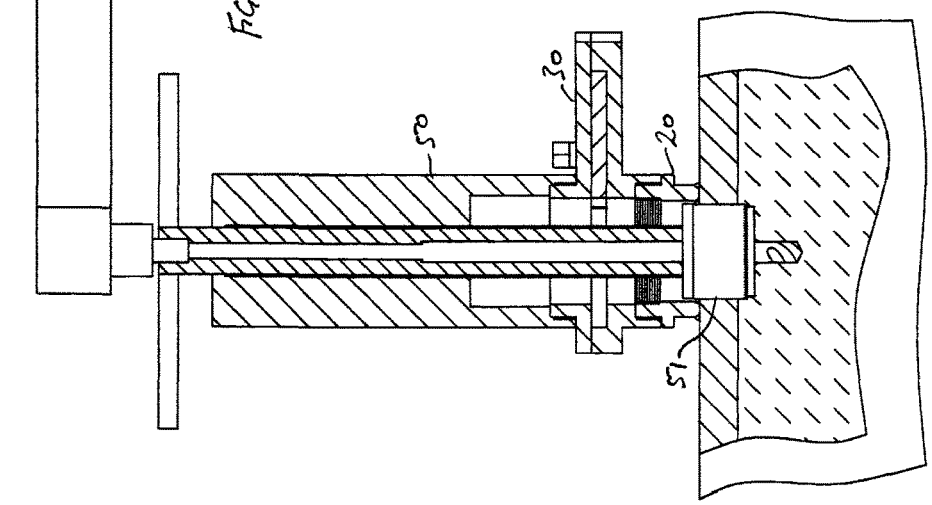
FIG. 14A
FIG. 14B

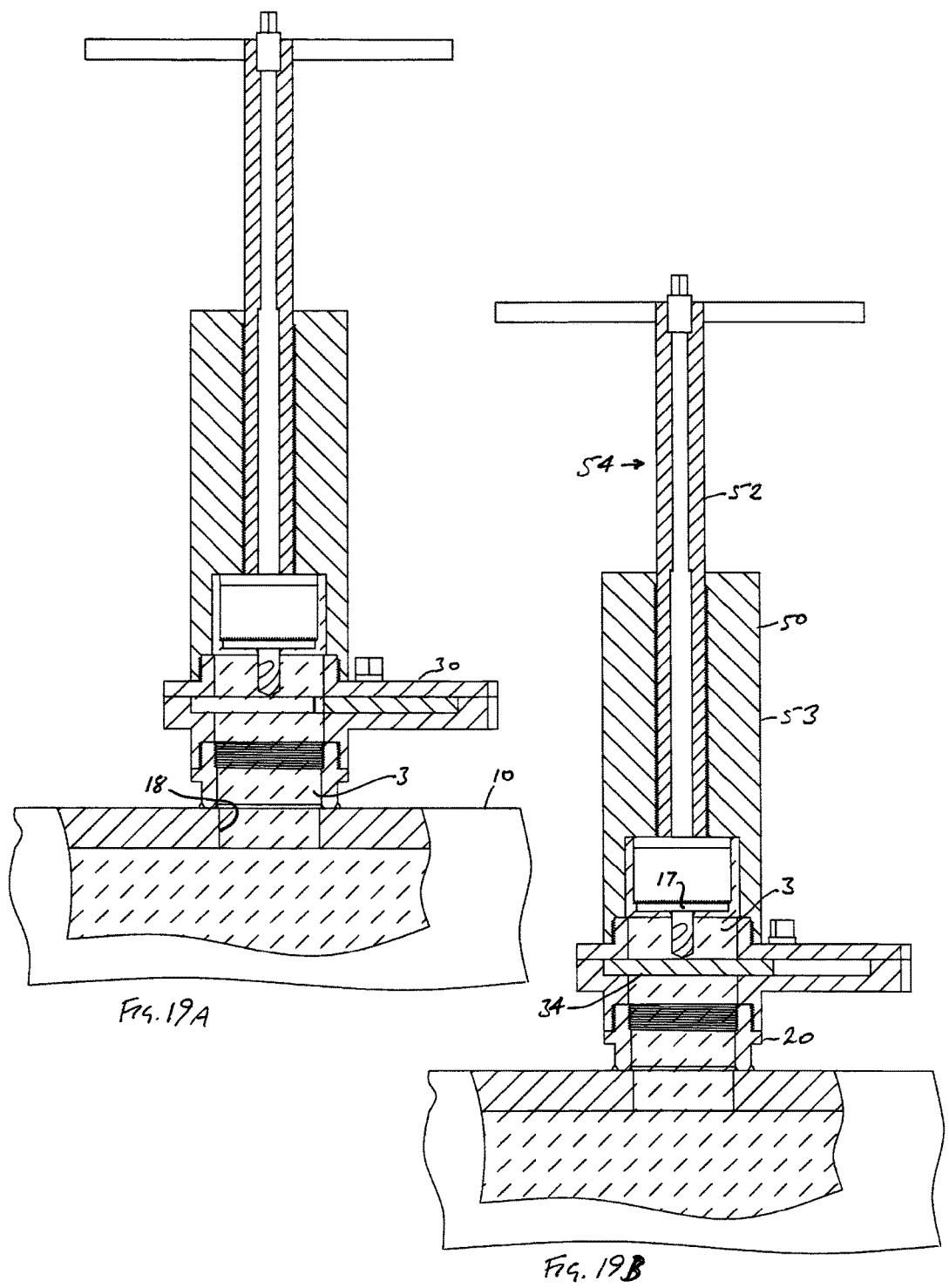

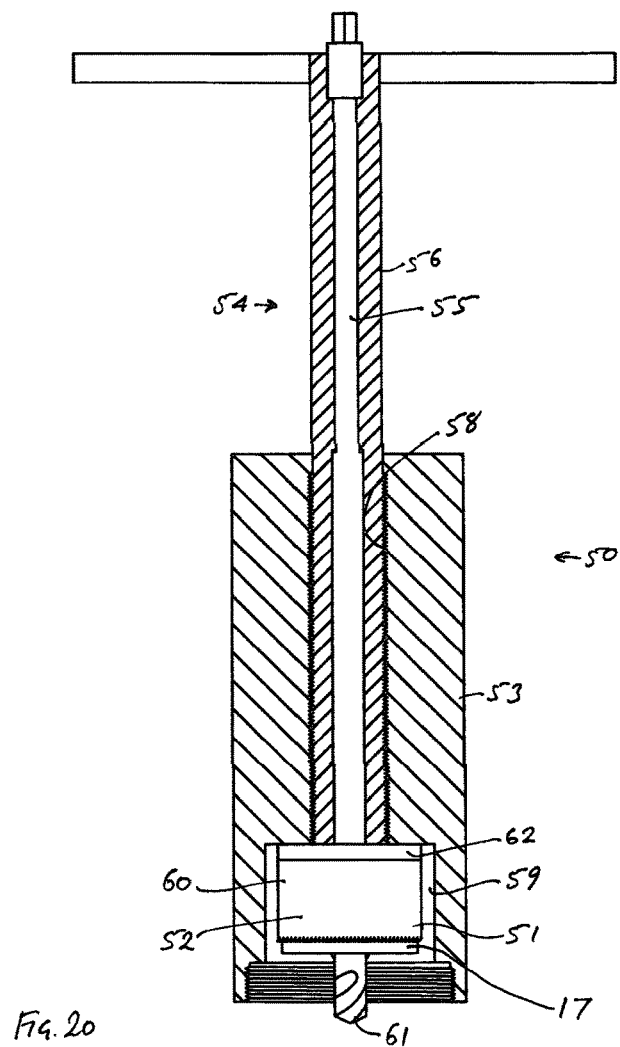
FIG. 20
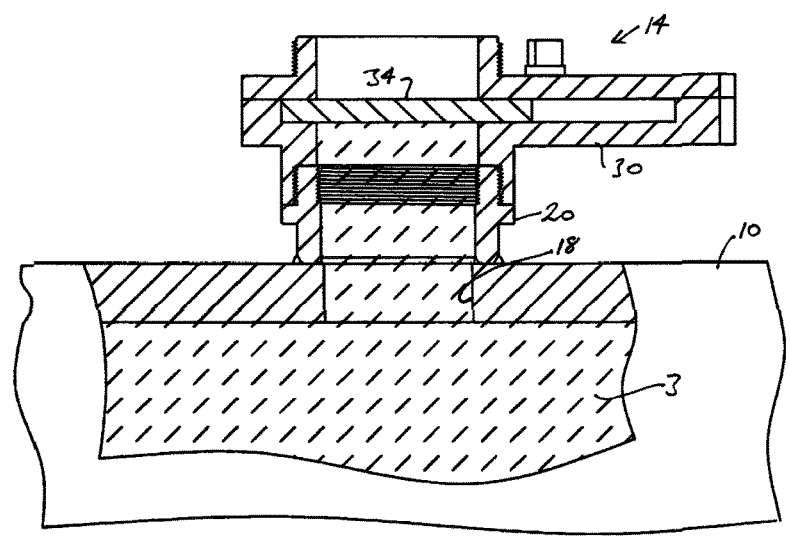

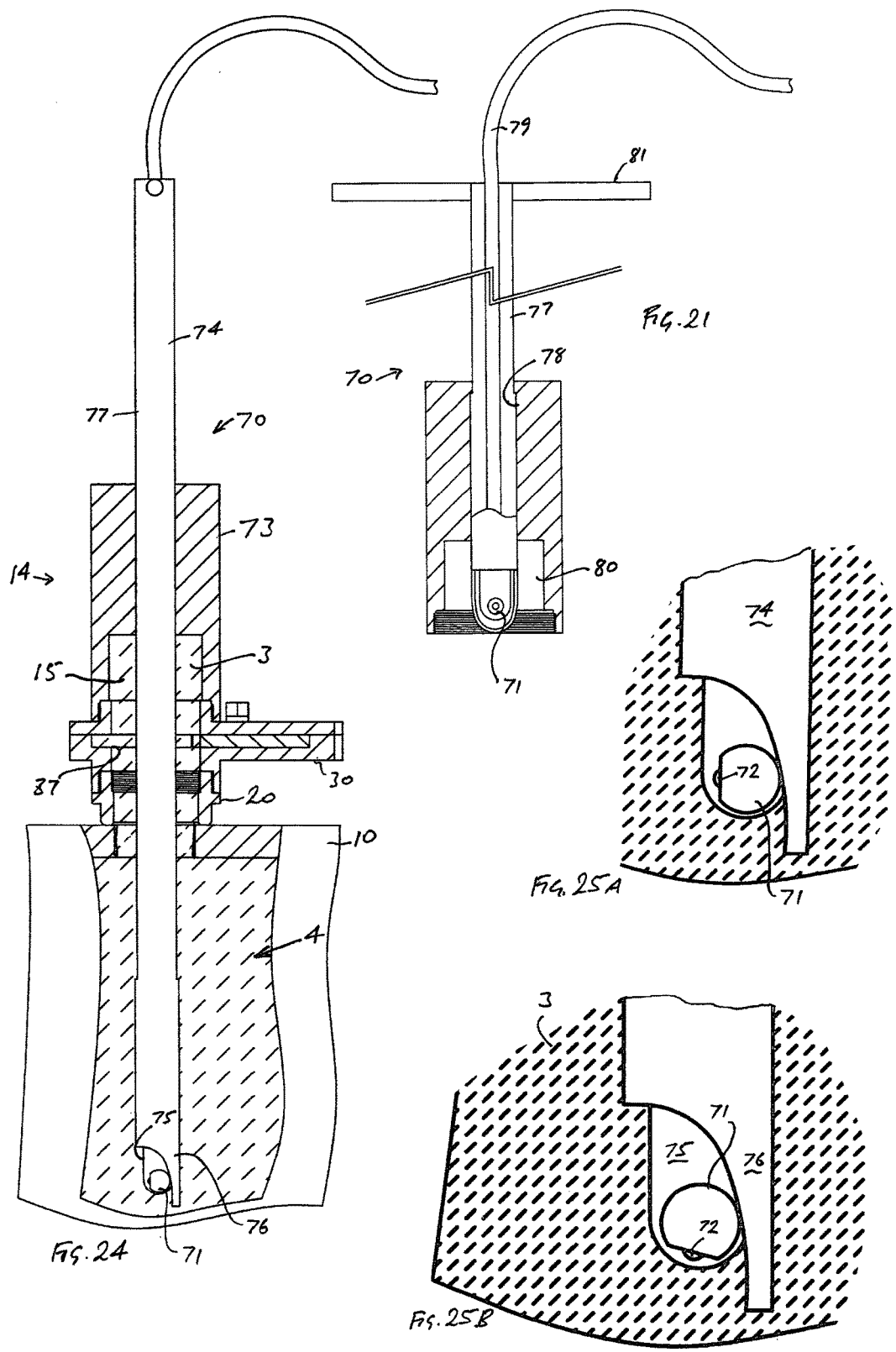

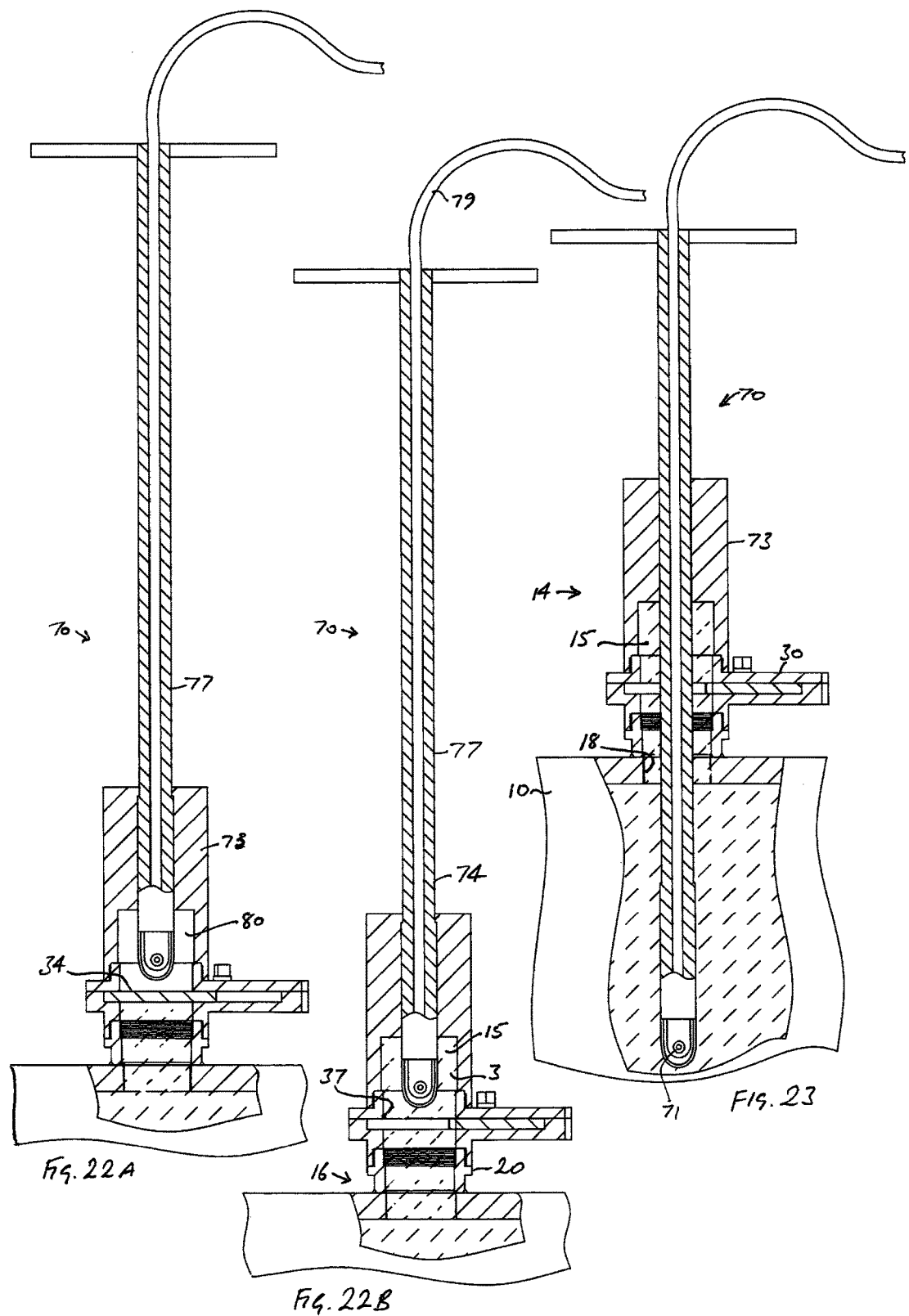

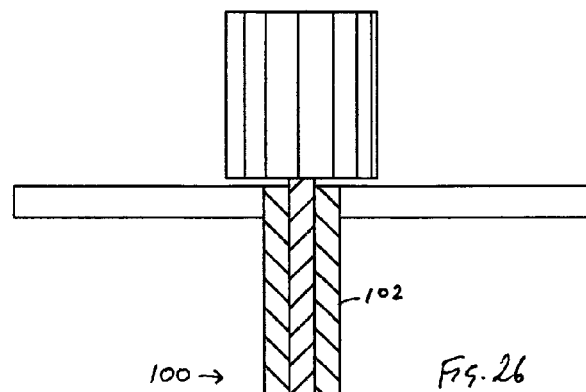
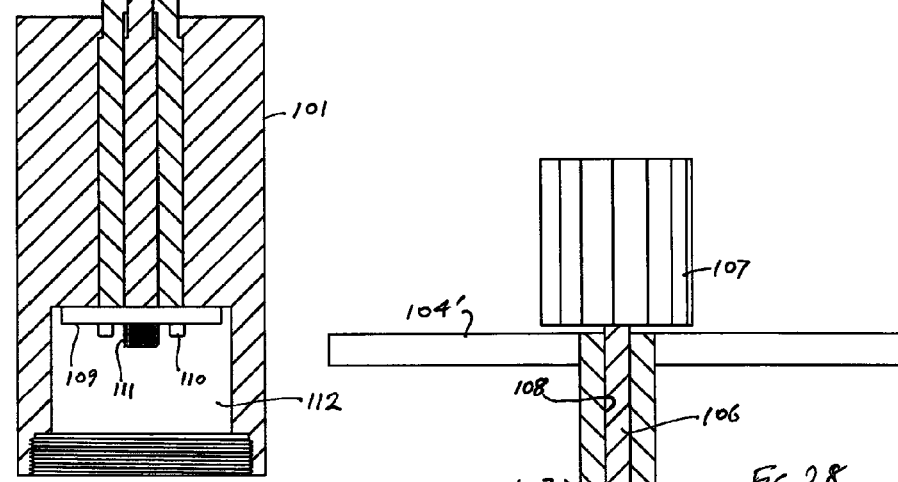
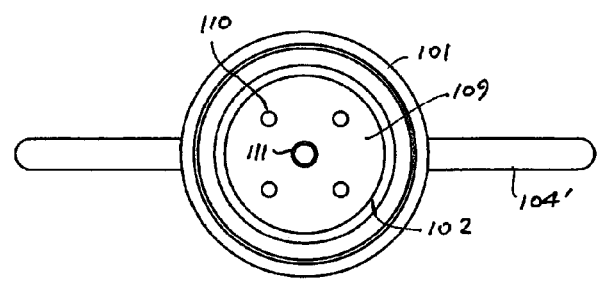
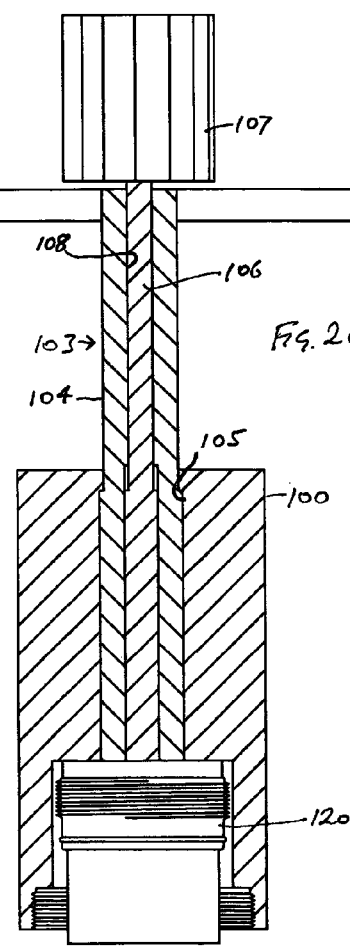
Fig. 26
Fig. 27
Fig. 28

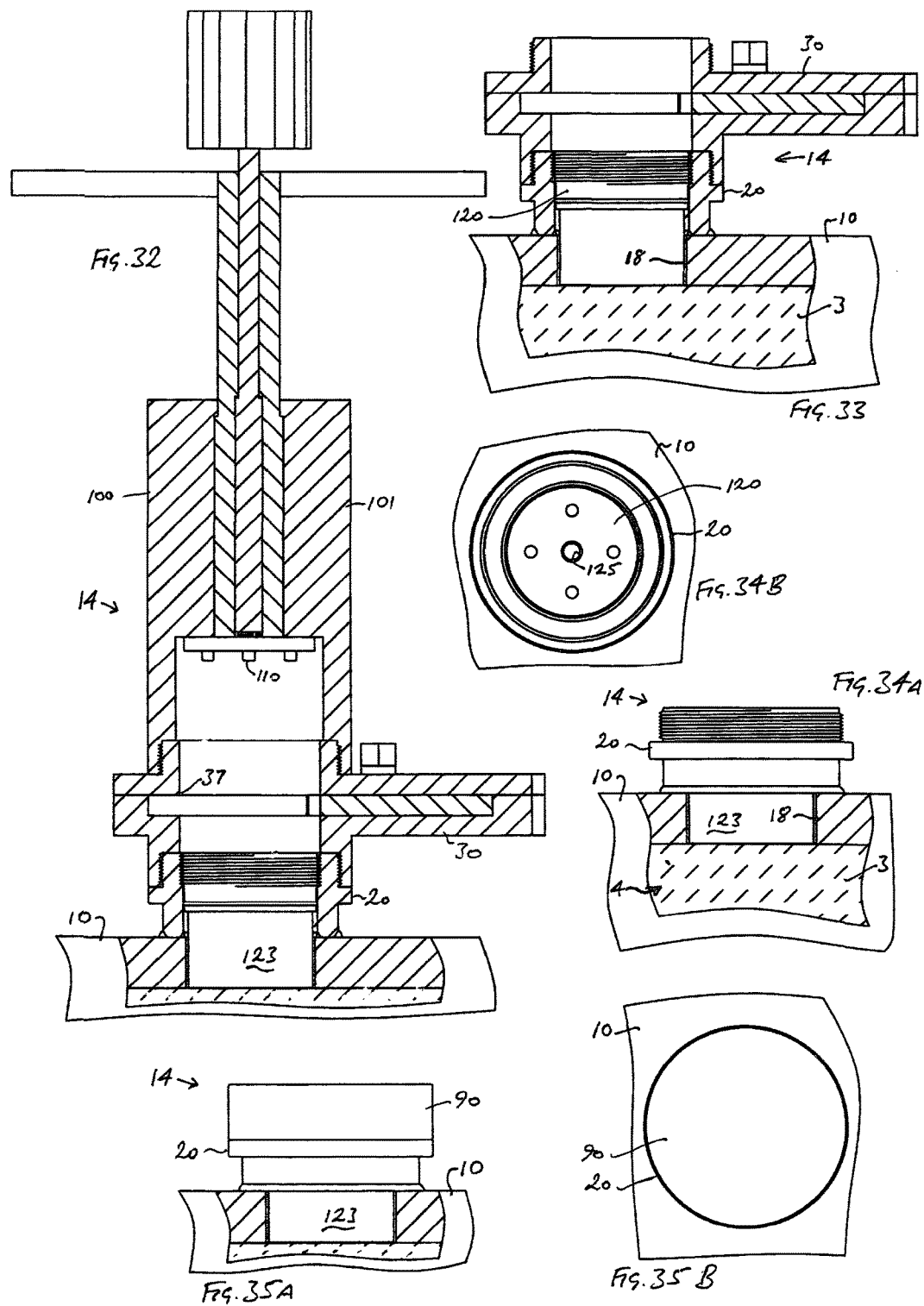

APPARATUS AND METHOD FOR INSPECTING FLOODED CAVITIES IN A FLOATING OFFSHORE INSTALLATION

This invention relates to the inspection of floating offshore installations, ships, and other floating or submerged marine structures.

Floating offshore installations (FOIs) include oil drilling platforms and similar structures which are intended for permanent or semipermanent deployment at a fixed location in the sea. Like ships, FOIs and other wholly or partially submersible structures are critically dependent for safe operation on the pressure integrity of their hull or outer shell. However, both ships and FOIs typically have many fluid penetrations of the hull below the waterline through which large volumes of water can flow for engine cooling, ballasting, and other purposes via large diameter pipes and valve gear (i.e. valves and associated apparatus) within the hull. In ships, these pipes normally terminate in compartments known as seachests which form recesses in the hull protected by gratings installed flush with the hull surface.

The interior surfaces of the seachests, other hull fluid penetrations and their connected pipework and valve gear where fitted define flooded cavities in fluid communication with the sea, so their interior (wetted) surfaces are protected where possible by specialised surface coatings to combat corrosion. Nevertheless, the walls of the pipework, seachests and other parts of these flooded cavities remain vulnerable to a range of failure conditions including corrosion, erosion or obstruction by particulates, mechanical failure of stressed or moving parts, and colonisation by marine organisms which can completely block pipework if allowed to proliferate. It is therefore necessary to inspect such cavities regularly to identify and remediate these conditions.

The functional status of the valve gear can be ascertained by closing selected ones of the valves and measuring the pressure drop across them. However, this gives only a momentary indication of the functional condition of the valve, and does not provide any warning of the extent of internal corrosion or other mechanical damage which could be expected to lead to failure in the months or years following the test. FOIs are usually inspected at intervals of up to 3 years and so it is important that the inspection identifies incipient failure conditions that may lead to failure during the 3-year period following the test. For this reason, visual inspection of valves and other vulnerable regions within the flooded cavities is strongly preferred.

The extent to which visual inspection is possible is however limited by the extreme difficulty of access to the flooded cavities. Pipework can be very large (up to 1 m diameter or even more) and so removal of valve gear and sections of pipework is often impractical, particularly since access to the exterior surface (i.e. the dry side) of the walls of the flooded cavities is very restricted in the confined spaces of the hull or shell of a ship or FOI. Despite the large size of much of the pipework, it is extremely difficult to access by remotely operated vehicles (ROVs), which are submersible vehicles carrying underwater cameras and other sensors, not least because a failed or trapped ROV would become an obstruction. ROVs are therefore used to survey the outer surface of the hull but seldom penetrate far inside its flooded cavities.

It is known to provide access ports having threaded closures and valves through which a borescope or remotely operated camera or other tools may be introduced into a flooded cavity to inspect or manipulate valve gear, sacrificial anodes, and other submerged parts. For example, KR20110012049U, US2009007833A1, KR100540079B1, JP48-91685U, KR20120016471A, and JP11-301570A disclose various means for sealing inspection ports and other penetrations in the walls of flooded cavities in ships and the like, while WO2010022993 A2 teaches a containment structure providing access to valve gear passing through a hull.

Where local inspection ports are not provided but the region to be inspected is close to the exterior surface of the hull, visual inspection may be carried out by means of an ROV or by a diver, for example as taught by U.S. Pat. No. 3,776,574, US2003106480A1, US2009147270A1, or U.S. Pat. No. 6,317,387B1. Means may be provided whereby a diver may more easily manipulate heavy gratings or other closures from outside the vessel, as taught for example by JP50-155795U and JP50-155796U. The diver may then enter the seachest and visually inspect or photograph any valve gear which is visible through the suction and discharge openings.

Such inspections are however dangerous for the diver and limited in scope, as well as being expensive and difficult to carry out in bad weather. In an alternative approach, it is known for example from JP53-31797U, JP51-20695U, JP51-22293U, JPS5519631A, NL7401259A, NO311561B1, JP2013047039A, KR20100092278A, and JP61-132487A to provide means by which seachests and other cavities may be isolated, drained or entered by inspection personnel from within the ship. It is also known to provide dry access to the exterior of a submerged hull, as taught by U.S. Pat. No. 5,513,930.

One problem which limits the use of inspection or entry ports is that space inside the hull at the exterior (dry) surfaces of the walls of the flooded cavities is often insufficient to accommodate the required valves or watertight hatches, especially since a heavy construction with some degree of redundancy is usually required in order to maintain acceptable hull integrity.

Where inspection ports or personnel entry means are not provided and the region of the flooded cavity requiring inspection is at some distance from its opening (suction or discharge) point to the sea, other inspection methods such as ultrasonic, eddy current, or magnetic particle nondestructive testing must be used. These techniques are effective in identifying cracking or reduction in plating thickness due to corrosion. However, it would be desirable to supplement these techniques by extending the visual inspection regime to regions of the flooded cavities which at present are impossible to access in order to obtain a more comprehensive and reliable assessment of their condition, especially in older ships or FOIs. It would further be desirable to implement a visual inspection regime which avoids the danger associated with underwater inspection of flooded cavities by divers.

It is accordingly the object of the present invention to make possible a more comprehensive visual inspection regime for flooded cavities in FOIs and the like without relying on divers.

Accordingly in its various aspects the present invention provides a method and a kit of parts as defined in the claims.

The parts are arranged to form a pressure retaining assembly including a connection body which is attached, preferably by welding to the wall of the flooded cavity in a position at which it is desired to carry out an inspection. The pressure retaining assembly defines a pressure retaining compartment within which an opening is formed in the wall of the cavity. A camera or other inspection tool can then be introduced via the pressure retaining compartment and the opening into the cavity. After carrying out the inspection, the fluid penetration can be sealed and opened for re-inspection at a future time.

The invention thus makes possible inspection of flooded cavities without the use of divers and at any desired location in a submerged structure. Optionally, the connection body may be sealed by a plug and a cap after carrying out the inspection, with the plug being introduced through a detachable valve apparatus. This provides a redundant seal which occupies minimal space within the structure, avoiding the need for an additional permanently installed valve at the penetration.

Further features and advantages will be evident from the illustrative embodiment which will now be described, purely by way of example and without limitation to the scope of the claims, and with reference to the accompanying drawings, in which:

FIG. 14A shows the penetrator apparatus in operation to form an opening in the wall of the cavity;

FIG. 14B is an enlarged view of part of FIG. 14A;

FIG. 18 shows two spring inserts;

FIGS. 19A and 19B show the penetrator apparatus in the retracted position after forming the opening, respectively with the valve open (FIG. 19A) and the valve closed (FIG. 19B);

FIG. 20 shows the penetrator apparatus after removal from the pressure retaining assembly;

FIG. 21 shows an inspection apparatus;

FIGS. 22A and 22B show in longitudinal sectional view the inspection apparatus attached to the valve apparatus to form part of the pressure retaining assembly, respectively with the valve closed (FIG. 22A) and open (FIG. 22B);

FIG. 23 shows the inspection apparatus with the camera advanced into the cavity;

FIG. 24 shows the inspection apparatus after panning the camera through 90°;

FIGS. 25A and 25B show the camera tilted about an axis transverse to the length axis of the shaft, respectively to side view and downward view positions;

FIGS. 26 and 27 are respectively a longitudinal sectional view and a bottom end view of a plug deployment apparatus;

FIG. 28 shows the plug attached to the plug deployment apparatus;

FIG. 32 shows the plug deployment apparatus after retracting the shaft assembly;

FIG. 33 shows the pressure retaining assembly after removal of the plug deployment apparatus from the valve apparatus;

FIGS. 34A and 34B show the pressure retaining apparatus comprising the connection body sealed with the plug after removal of the valve apparatus, respectively in side view (FIG. 34A) and top view (FIG. 34B); and FIGS. 35A and 35B show the cap attached to form part of the pressure retaining apparatus, respectively in side view (FIG. 35A) and top view (FIG. 34B).

Corresponding reference numerals indicate the same features in each of the figures.

Figure 1:
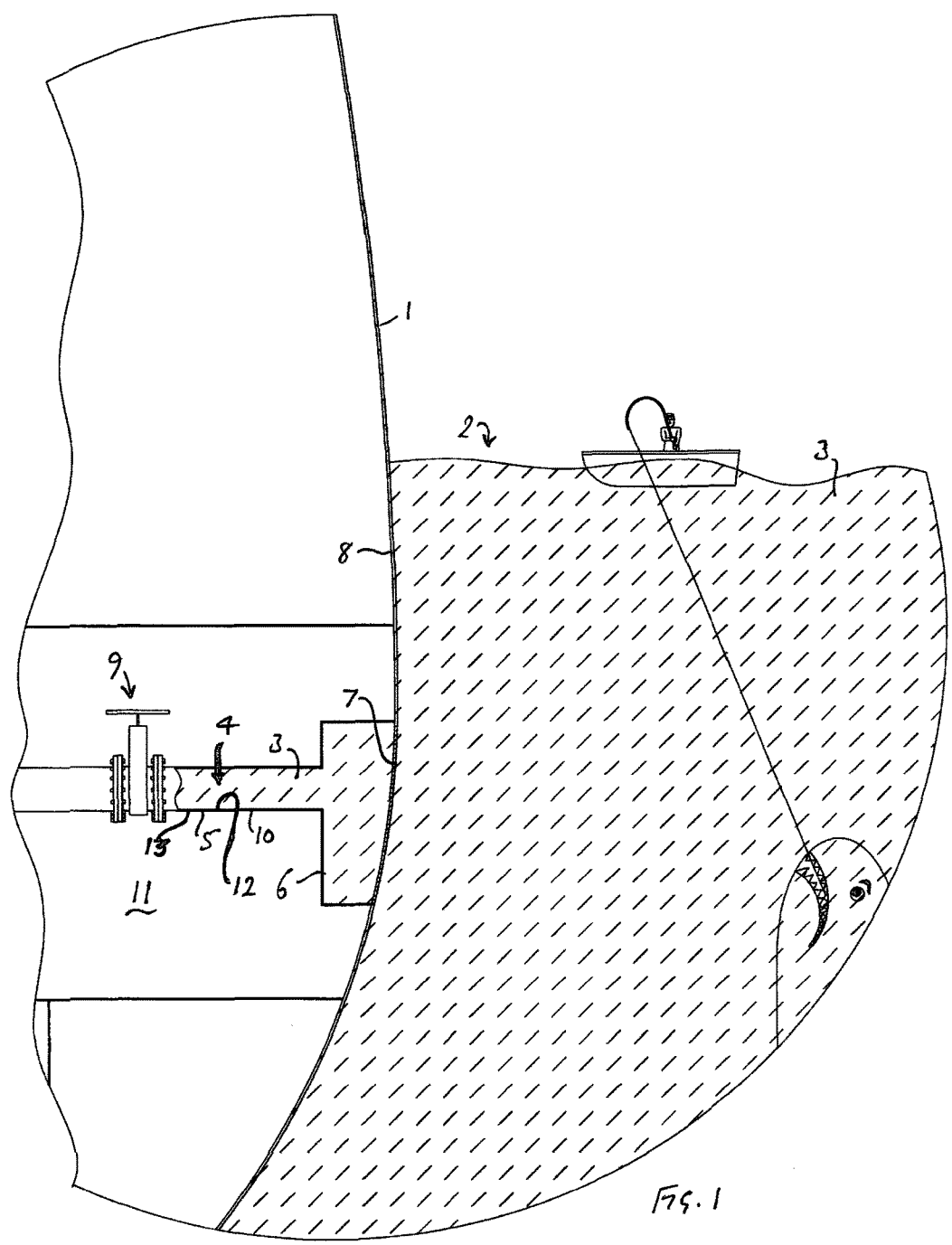
FIG. 1 shows a flooded cavity within a partially submerged structure.
Figures 4A, 4B:
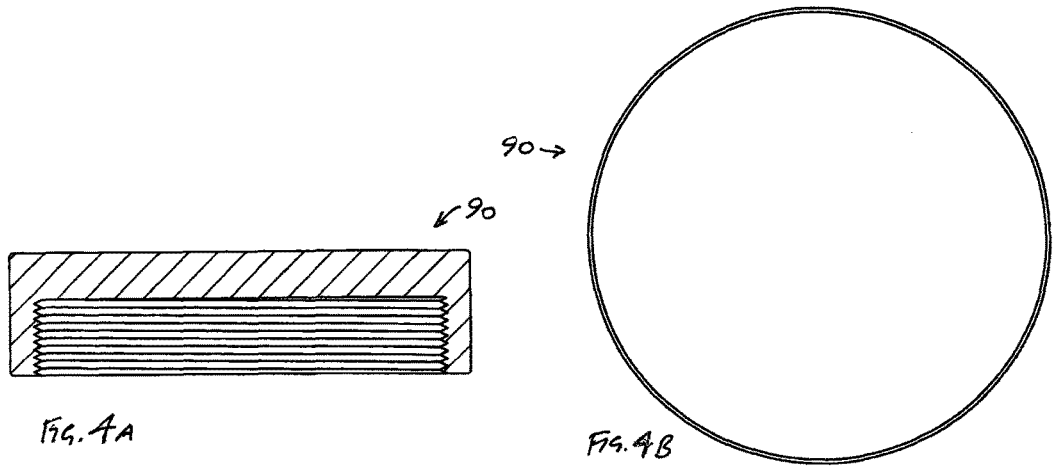
FIGS. 4A and 4B are respectively a longitudinal sectional view and a top view of a cap.

FIG. 1 shows a structure 1 which is floating and partially submerged in a body 2 of sea water 3 so that a cavity 4 formed by a pipe 5, suction box or seachest 6 is flooded with water via a grating 7 in the hull or shell 8 of the structure through which the body of water is in fluid communication with the cavity. In the illustrated example, it is desired to carry out an inspection on large diameter valve gear 9 which is installed on the pipe 5 forming for example a suction inlet or outlet flowpath for ballast or cooling water. The wall 10 of the pipe defining the cavity 4 excludes the water 3 in the cavity from the dry interior space 11 within the structure, the wall having a wet side 12 exposed to fluid pressure within the cavity and an opposite, dry side 13 within the interior space 11 and exterior to the cavity.

A kit of parts includes a connection body 20, a valve apparatus 30, a penetrator apparatus 50 comprising a holesaw 51, an inspection apparatus 70 comprising a camera 71, a plug deployment apparatus 100, a plug 120, and a cap 90, as further described below.

Figures 2A, 2B:
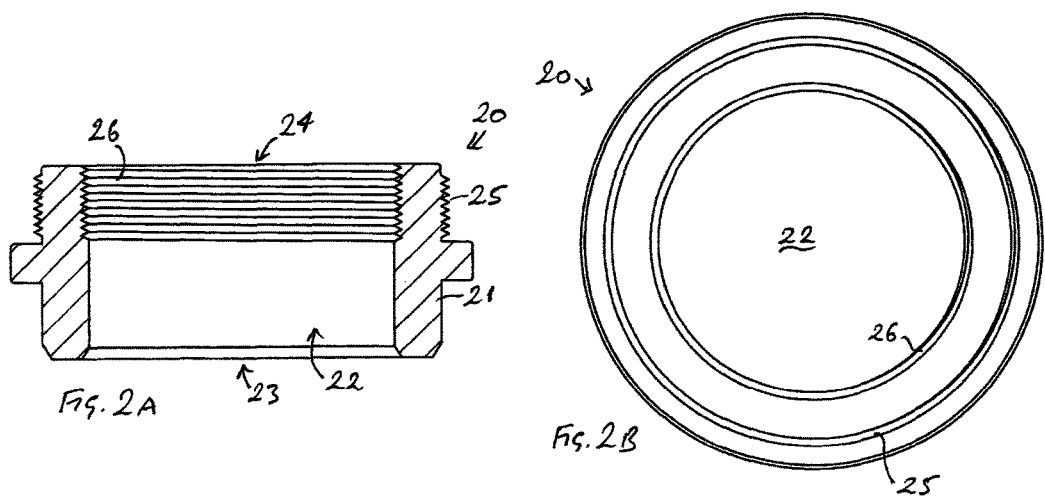
FIGS. 2A and 2B are respectively a longitudinal sectional view and a top view of a connection body.
Figures 3A, 3B:
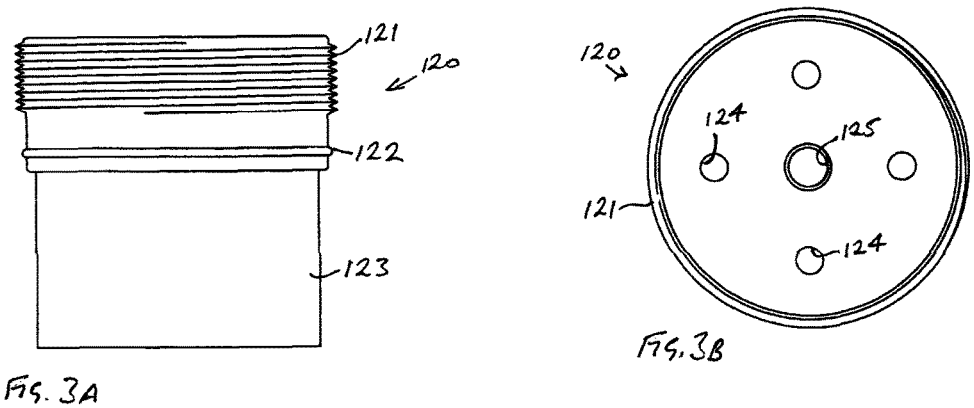
FIGS. 3A and 3B are respectively a side view and a top view of a plug with a sacrificial anode.

Referring to FIGS. 2A and 2B, the connection body 20 comprises a short stainless steel cylinder 21 having a straight bore 22 defining axially aligned first 23 and second 24 intercommunicating apertures, with male 25 and female 26 threads at the second aperture.

Figure 5:
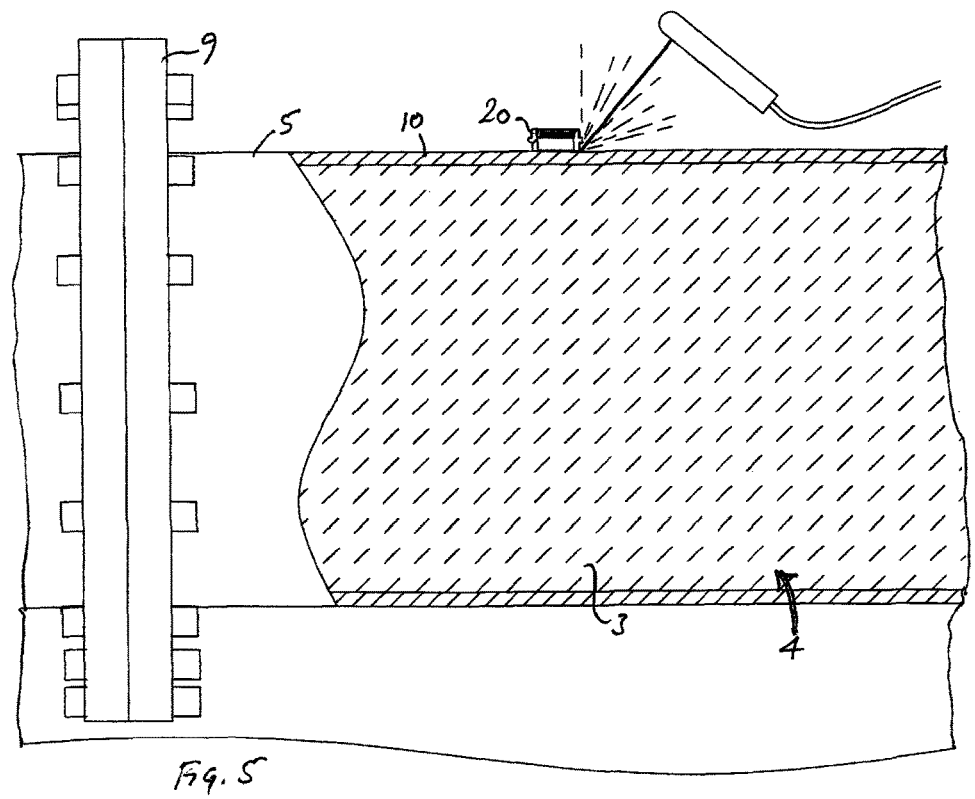
FIG. 5 shows the connection body being welded to the wall of the cavity.
Figure 6:
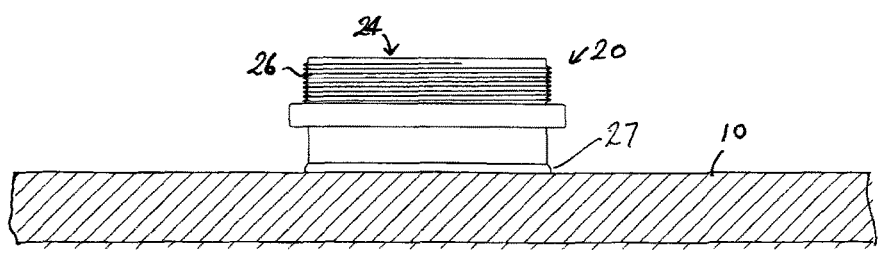
FIG. 6 shows the connection body attached to the wall of the cavity after welding in its use position.

The connection body 20 is sealingly fixed at its first aperture 23 to the dry side of the wall of the flooded cavity, preferably by welding as shown in FIG. 5. In the illustrated example the connection body is welded both internally and externally at the first aperture leaving it permanently fixed to the wall 10 of the cavity in its use position by two weld beads 27 as shown in FIG. 6. Respective ones of the other parts are then connected together with the connection body as required to form in their respective use positions a pressure retaining assembly 14 defining a pressure retaining compartment 15, with the connection body forming the base portion 16 of the assembly.

In the illustrated embodiment, the respective parts are releasably connected together by screwing them onto the male thread 25 at the second aperture of the connection body. Other connection means may be used if it is desired to fit the parts without rotating them. Although not shown, seals are preferably provided to ensure a pressure tight connection.

Figure 7:
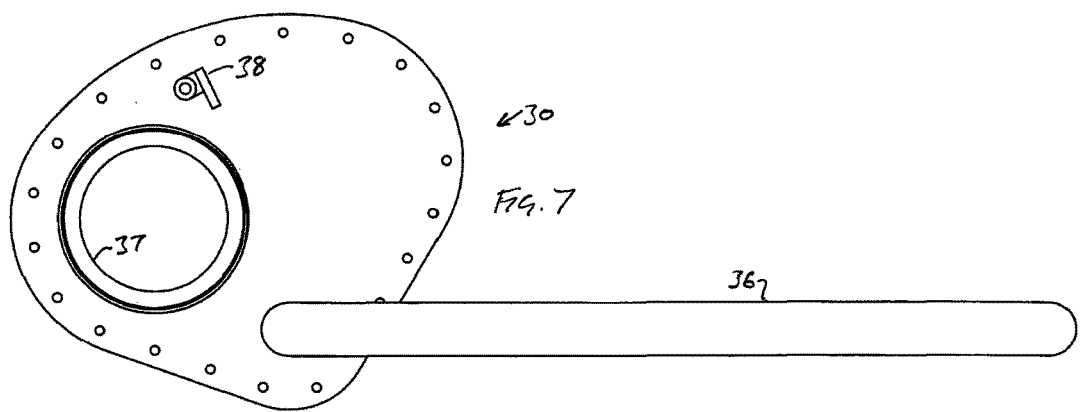
FIG. 7 is a top view of a valve apparatus.
Figure 8A:
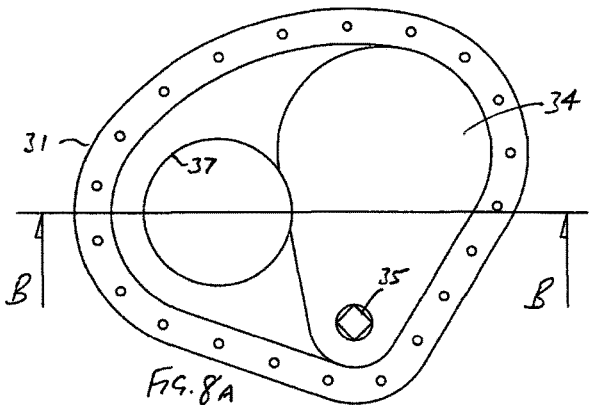
FIGS. 8A and 9A show the interior of the valve apparatus with the top plate removed, respectively in the open (FIG. 8A) and closed (FIG. 9A) positions.
Figure 8B:
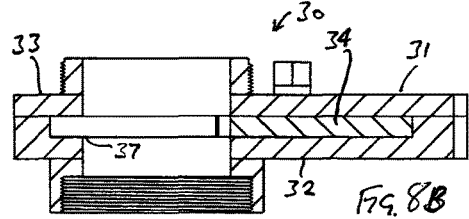
FIGS. 8B and 9B are longitudinal sections at lines B-B of FIGS. 8A and 9A respectively.
Figure 9A:
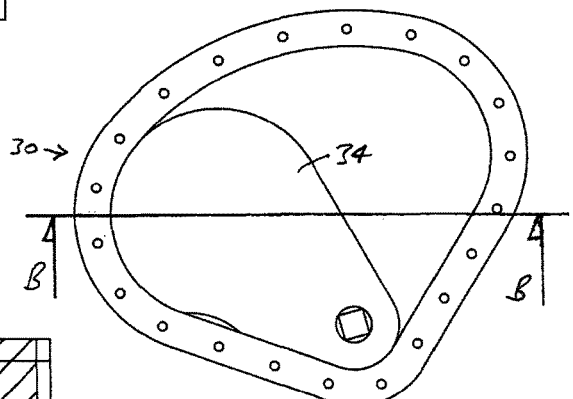
Figure 9B:
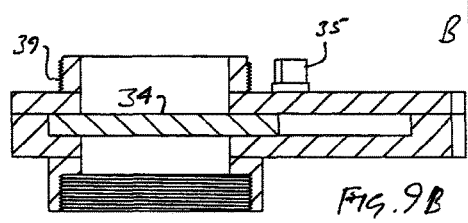
Figure 11:
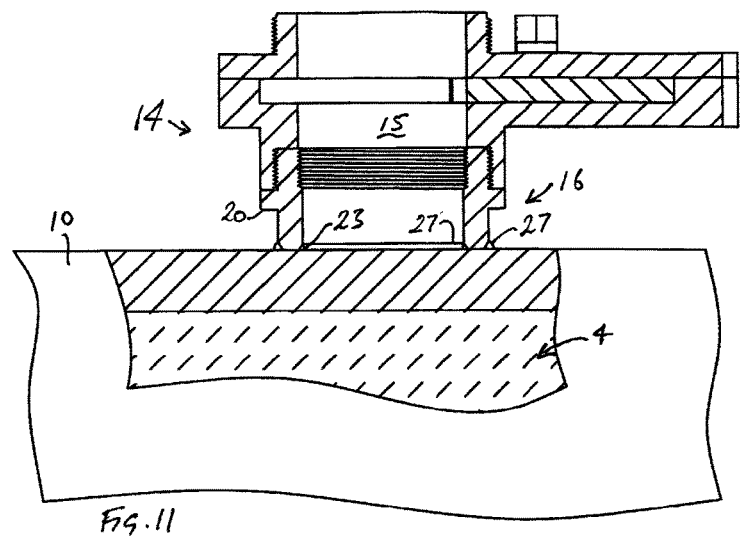
FIGS. 10 and 11 show the valve apparatus screwed onto the connection body to form a pressure retaining assembly, respectively in side and longitudinal sectional view.
Figure 10:
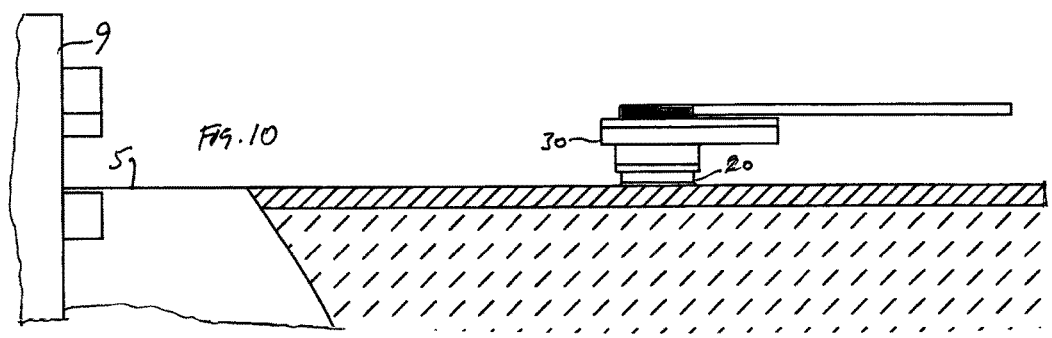
Figure 12:
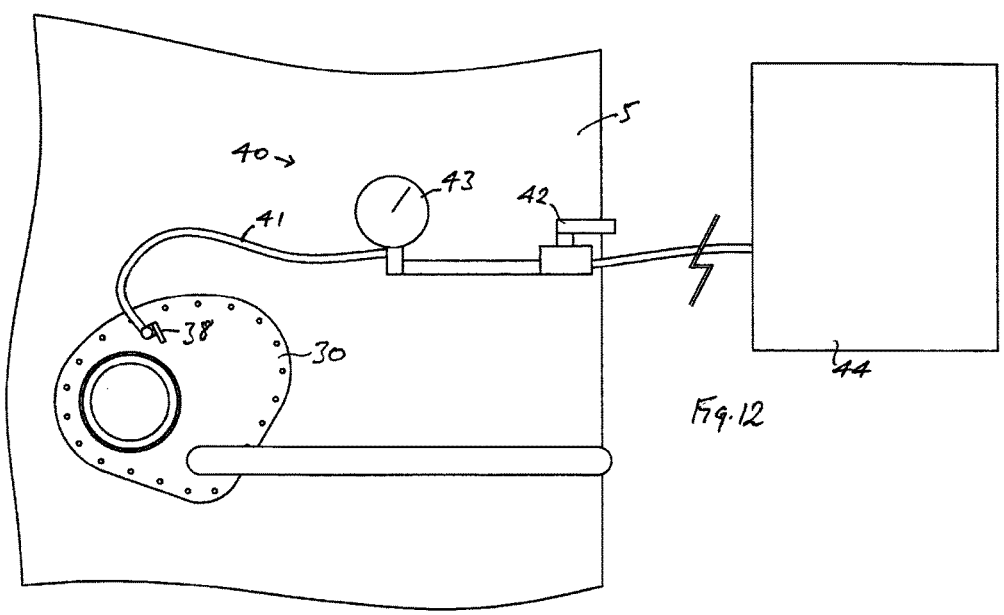
FIG. 12 shows the pressure retaining assembly being pressure tested before attaching further parts of the assembly.
Figure 13A:
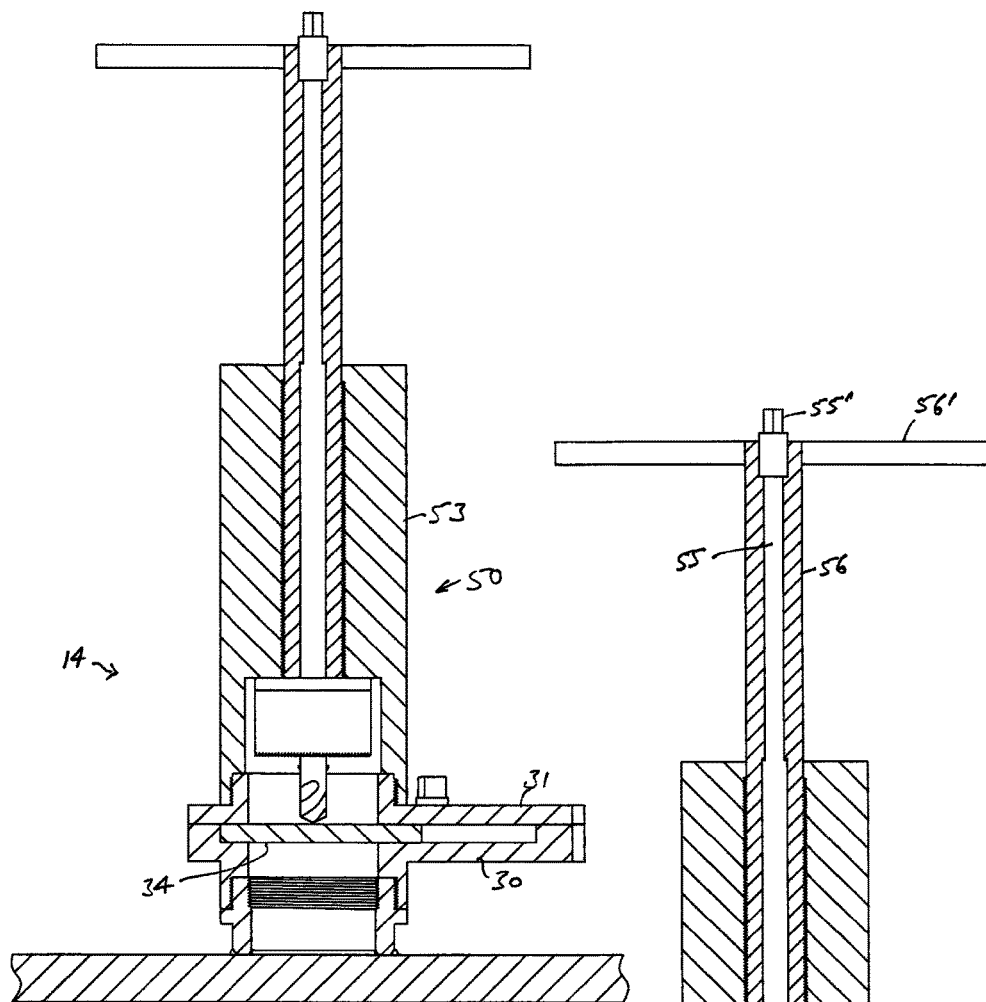
FIGS. 13A and 13B show in longitudinal sectional view a penetrator apparatus attached to the valve apparatus to form part of the pressure retaining assembly, respectively with the valve closed (FIG. 13A) and the valve open (FIG. 13B)
Figure 13B:
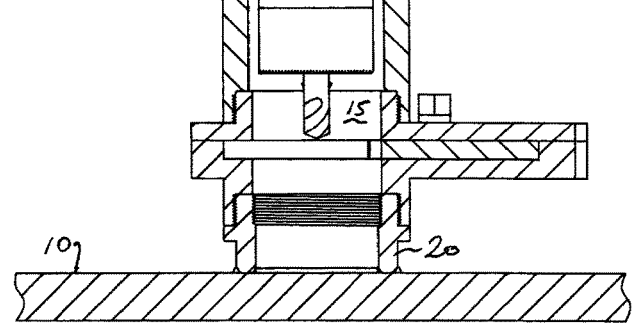
Figure 15:
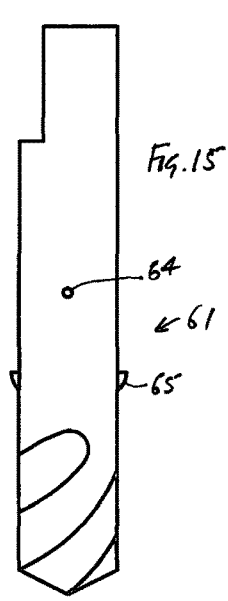
FIG. 15 shows the pilot drill of a holesaw forming part of the penetrator apparatus.

Referring to FIGS. 7-9, the valve apparatus 30 is a sandwich valve assembly, comprising a valve body 31 with lower 32 and upper 33 plates defining a cavity containing the valve 34, which is a flat plate operable by rotating the spindle 35 with handle 36 to selectively open (FIGS. 8A, 8B) and close (FIGS. 9A, 9B) the valve orifice 37 so as to control fluid communication via the second aperture 24 of the connection body 20 when it is attached to the connection body in its use position. The valve body also includes a small secondary valve assembly 38 which closes a fluid passageway communicating with the pressure retaining compartment 15, which extends through the bore 22 of the connection body when the valve apparatus is connected in its use position by screwing it onto the connection body as shown in FIGS. 10 and 11.

After connecting the valve body 31 to the connection body 20, a pressure testing apparatus 40 comprising a compressed air hose 41, a valve 42 and a pressure gauge 43 is used to connect the pressure retaining compartment 15 via the secondary valve assembly 38 to a compressor or other pressure source 44. The pressure retaining compartment 15 is then pressurised to a test pressure to test the integrity of the weld and the remainder of the assembly. Magnetic particle or other nondestructive testing techniques may also be used to verify the weld.

After pressure testing the valve and connection body, the penetrator apparatus 50 is screwed onto the male thread 39 on the valve body. The penetrator apparatus comprises a penetrator tool 52 and a penetrator body 53, the penetrator tool including a shaft assembly 54 having an inner shaft 55 which is sealingly received within an outer shaft 56 and driven in rotation by a suitable manual or motorised drive means such as an air tool 57. The outer shaft is sealed, e.g. by means of O-ring seals (not shown) in a threaded bore 58 in the penetrator body. The penetrator body defines a cavity 59 which in its use position forms part of the pressure retaining compartment 15 and which in a retracted position of the penetrator tool receives the holesaw 51, comprising a cylindrical blade 60 and a pilot drill bit 61 which are mounted on a base 62 fixed to the distal end of the inner shaft.

Advantageously, the penetrator tool may be arranged to remove a portion 17 of the wall 10 of the cavity to form the opening 18, which provides a neat penetration with minimal debris. Further advantageously, it may be provided with a retaining means which is arranged to retain the removed portion 17 so that it can be recovered together with the tool. This prevents the removed portion of the wall from falling into the cavity and obstructing the pipework or damaging valve or pump gear.

Referring to FIGS. 15-18, this is achieved in the illustrated example by maching a narrow cavity 62 in the shank of the pilot drill bit 61 above its helically fluted distal end portion. The retaining means comprises a pair of spring inserts 63 made from spring steel, beryllium copper or the like are inserted into the cavity and fastened with a pin 64. The distal ends of the inserts extend outwardly from the shank of the drill to define forwardly directed ramped surfaces 65 and oppositely directed, backwardly facing abutment surfaces 66.

Figure 18A:
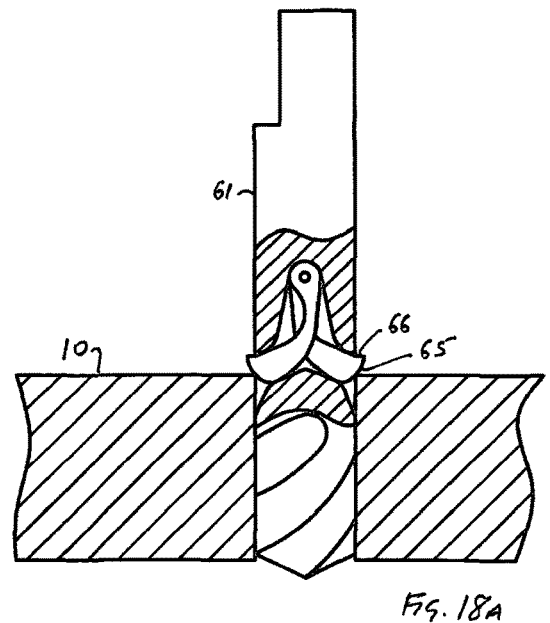
FIGS. 18A, 18B and 18C show the action of the spring inserts in use as the pilot drill is advanced through the wall of the cavity.
Figure 18B:
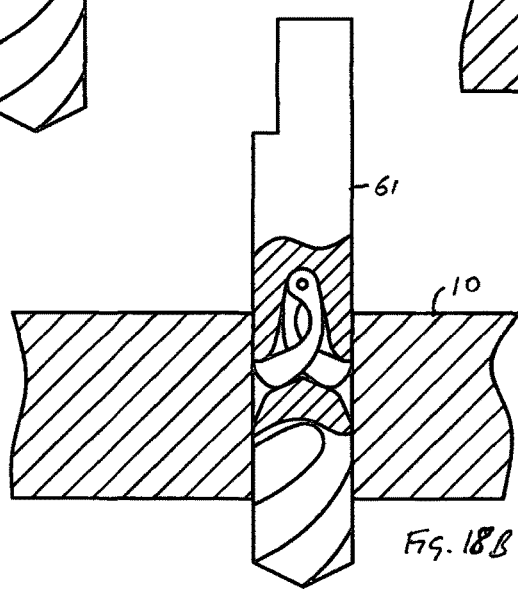
Figure 17:
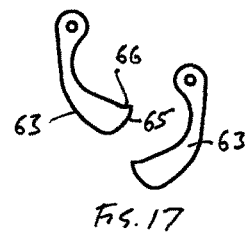
Figure 16:
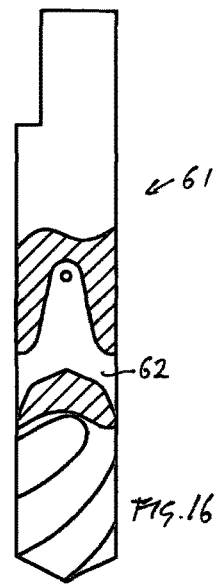
FIG. 16 shows the pilot drill partly cut away to reveal its internal structure.
Figure 18C:
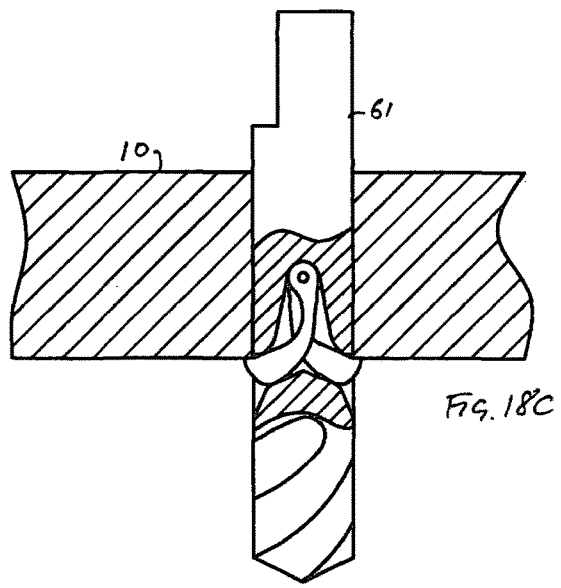

After mounting the penetrator body 53 on the valve body 31, the air tool 57 is releasably engaged with the square drive profile 55' on the inner shaft 55 to drive the holesaw in rotation while the handle 56' of the outer shaft 56 is rotated to advance the pilot drill and holesaw blade through the open valve orifice 37 and the connection body into the wall 10 of the cavity so that the holesaw cuts out a circular portion 17 resembling a thick washer from the wall of the cavity within the first aperture 23 (FIGS. 14A, 14B). As the pilot drill penetrates the wall, the spring inserts 63 are compressed and then released to capture the washer on the pilot drill as shown in FIGS. 18A, 18B, 18C.

In this manner the penetrator tool is operated within the pressure retaining compartment 15 to form an opening 18 in the wall of the flooded cavity within the first aperture 23, so as to establish fluid communication between the flooded cavity and the pressure retaining compartment via the opening. After forming the opening 18, the penetrator tool 52 is retracted to withdraw the retained washer 17 from the opening 18, and then is withdrawn together with the washer back through the connection body and the valve orifice to a retracted position (FIG. 19A) before closing the valve to isolate the penetrator tool 52 from fluid pressure within the pressure retaining compartment (FIG. 19B). The penetrator body is then unscrewed and removed together with the retained washer 17 from the valve body leaving the opening 18 sealed by the valve 34 (FIG. 20).

Referring to FIGS. 21-25, the inspection apparatus 70 comprises an inspection body 73 and an inspection tool 74 comprising a camera 71 with a lens 72. The camera is moveably mounted in a transparent pressure resistant casing 75 within a protective shroud 76 at the distal end of a shaft 77 which is sealingly received for both rotational and axial motion in a bore 78 of the body 73, the camera being connected to power, display and control means via a cable 79 passing through the shaft 77. With the inspection tool in a retracted position, the inspection body 73 is screwed onto the valve body 31 in its use position as shown in FIG. 22A. In this position the camera is received in a cavity 80 in the inspection body which when the valve 34 is open forms part of the pressure retaining compartment 15, so that by closing the valve 34 the inspection tool can be selectively isolated from fluid pressure within the pressure retaining compartment.

The valve is then opened (FIG. 22B) and the inspection tool is slidingly advanced so that it extends through the open valve orifice 37, the connection body 20 and the opening 18 into the flooded cavity 4 to an extended position (FIG. 23). In this position the camera can be panned by rotating shaft 77 using handles 81 (FIGS. 23, 24), and can also be electromechanically tilted (FIGS. 25A, 25B) so that it is has an unrestricted field of view. For use in turbid water, an infra red camera can be employed, or multiple sequential images can be averaged to remove signal data representing moving debris so as to leave a clearer image of fixed objects, as known in the art.

After inspecting the cavity; the inspection tool 74 is retracted from the extended position and withdrawn back through the opening 18, the connection body 20 and the valve orifice 37 before closing the valve 34. The inspection body 73 can then be unscrewed and removed from the valve body 31.

Referring to FIGS. 3A and 3B and FIGS. 26-34, the plug deployment apparatus 100 comprises a plug deployment body 101 and a plug deployment tool 102. The tool 102 includes a shaft assembly 103 with an outer shaft 104 which is sealingly received for rotational and sliding axial motion in a bore 105 of the body, and an inner shaft 106 with a knob 107, the inner shaft being sealingly received for rotational and sliding axial motion in a bore 108 of the outer shaft. The outer shaft terminates in a flat plate 109 having four studs 110 arranged around the projecting distal end of the inner shaft, on which a thread 111 is formed. In the retracted position as shown in FIG. 26 the plate 109 is received in a cavity 112 within the plug deployment body 101 which forms part of the pressure retaining compartment 15 in its use position.

The plug 120 comprises a solid cylindrical block of stainless steel with a male thread 121 and an O-ring seal 122. A protective sacrificial anode 123 of zinc or the like is attached in electrically conductive relation to its lower end face. The upper end face of the plug has four smooth sockets 124 arranged around a central threaded socket 125. The plug is inserted into the cavity 112 in the plug deployment body so that the studs 110 engage in the sockets 124, and the knob 107 is rotated to engage the threaded end 111 of the inner shaft in the threaded socket 125 so that the plug 120 is drawn onto the studs 110 and retained in rotationally fixed relation to the end of the outer shaft 104.

Figures 29A, 29B:
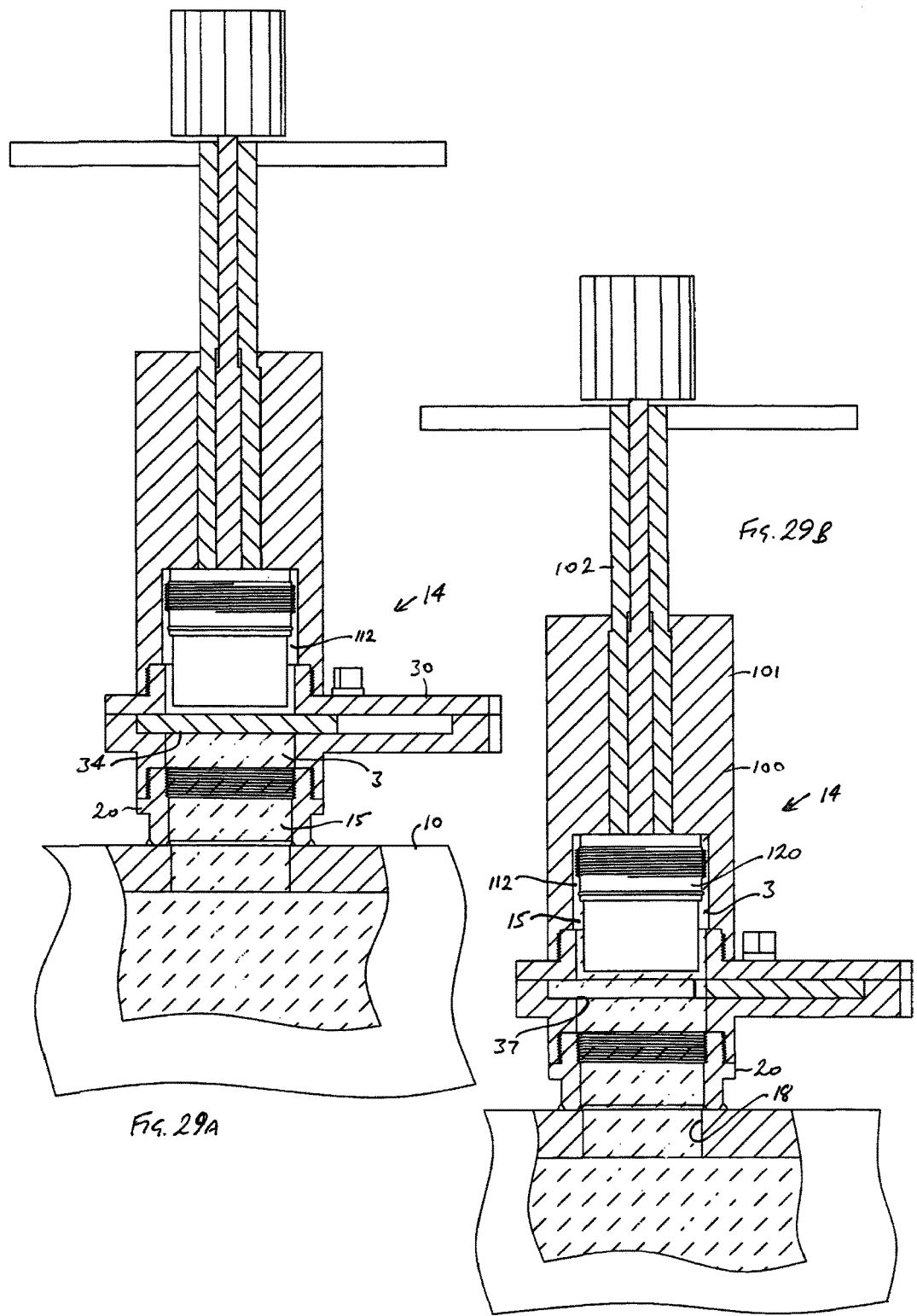
FIGS. 29A and 29B show the plug deployment apparatus attached to the valve apparatus to form part of the pressure retaining assembly, respectively with the valve closed (FIG. 29A) and the valve open (FIG. 29B)
Figures 30, 31:
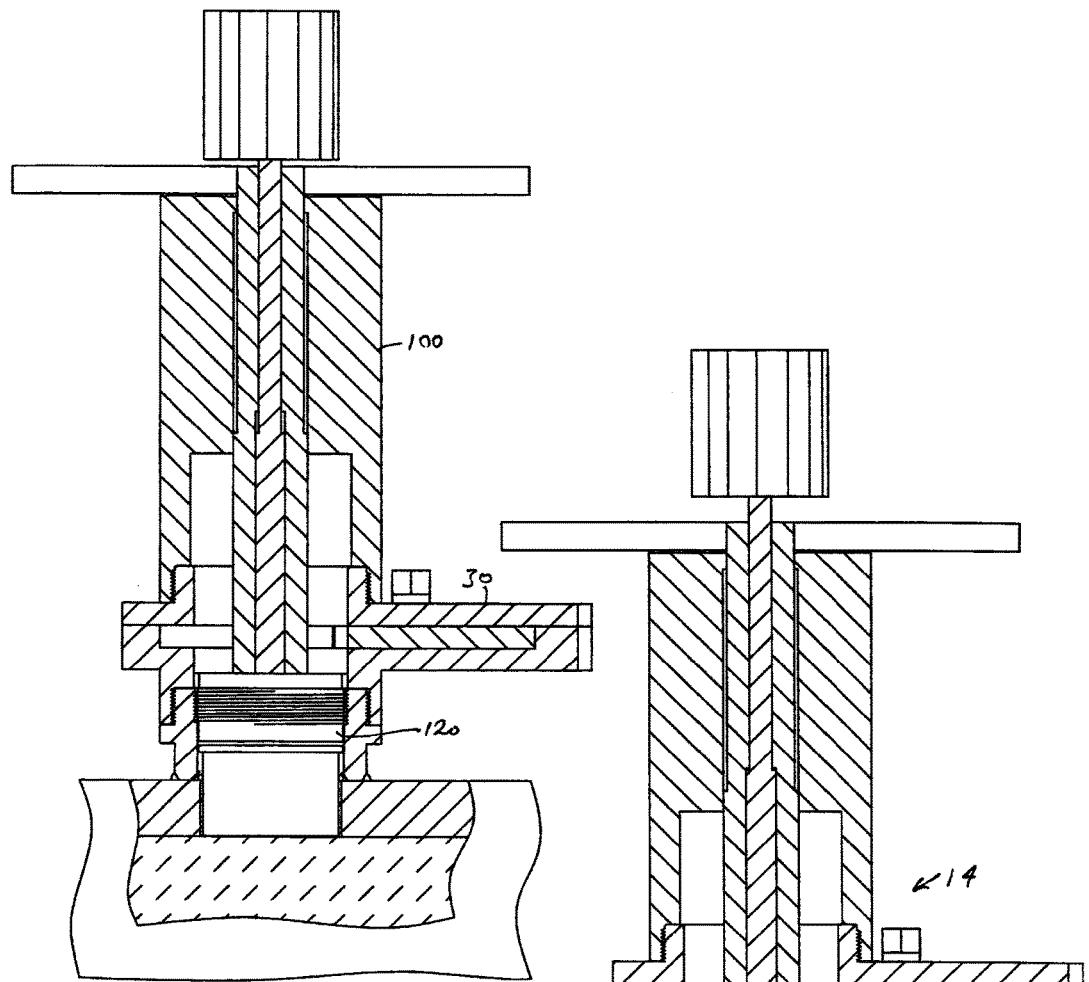
FIG. 30 shows the plug deployment apparatus after engaging the plug with the connection body.
FIG. 31 shows the plug deployment apparatus after disengaging the inner shaft from the plug.

The plug deployment body 101 is then screwed onto the valve body 31 so that in its use position the closed valve 34 isolates the plug 120 and the plug deployment tool 102 from fluid pressure within the pressure retaining compartment 15 (FIG. 29A). The valve 34 is then opened (FIG. 29B) so that the plug is exposed via the open valve orifice 37 to fluid pressure within the pressure retaining compartment 15 before slidingly advancing the shaft assembly 103 through the plug deployment body so that the plug 120 together with its protective anode 123 is advanced through the open valve orifice 37 to engage its male thread 121 with the female thread 26 in the connection body 20. The handle 104' of the outer shaft 104 is then rotated to screw the plug into the connection body, compressing the O-ring seal 122 so that the plug is sealingly engaged with the connection body to form part of the pressure retaining assembly 14 (FIG. 30). The handle 104' is then held still while the knob 107 is rotated to unscrew the inner shaft 106 from the plug (FIG. 31) before axially retracting the shaft assembly to detach the studs 110 from the plug (FIG. 32). The plug deployment body can then be unscrewed and removed from the valve body (FIG. 33), after which the valve apparatus 30 is also removed, leaving the connection body 20 sealed by the plug 120 (FIGS. 34A, 34B).

In this position the protective anode 123 extends through the opening 18 in the wall 10 of the flooded cavity 4 so that it is exposed to the water 3 in the flooded cavity and connected electrically to the wall 10 of the cavity via the interengaged threads of the plug and the connection body and the weld bead between the connection body and the wall, forming a galvanic circuit which protects the cut surfaces of the wall from corrosion at the periphery of the opening 18. This solves the problem of corrosion of the wall 10 at the opening which would otherwise result from penetration of the protective coating at the wet side of the wall. Advantageously, the anode 123 is removed together with the plug 120 so that it can very easily be checked and renewed if required each time the cavity 4 is inspected.

Referring to FIGS. 4A and 4B and FIGS. 35A and 35B, a female threaded cap 90 with a suitable seal (not shown) can then be screwed onto the male thread 25 of the connection body 20 to provide a double (redundant) barrier, so that the connection body is sealed with both the plug and the cap.

At the time of the next inspection, the cap 90 is removed and the valve apparatus 30 re-attached to the connection body 20. The plug deployment apparatus 100 is then screwed onto the valve body (FIG. 32) before advancing the plug deployment tool again through the open valve orifice and rotating the knob 107 to engage the threaded end 111 of the inner shaft with the plug, drawing the studs 110 of the outer shaft 104 into the smooth sockets 124 (FIG. 30). The outer shaft 104 is then rotated to unscrew the plug before withdrawing the plug deployment tool together with the plug back through the valve orifice to the retracted position (FIG. 29B) and closing the valve 34 (FIG. 29A). The plug deployment apparatus can then be removed together with the plug 120 from the pressure retaining assembly 14 leaving the opening 18 sealed by the valve 34 as shown in FIG. 20 before re-connecting the inspection apparatus 70 and carrying out a further inspection of the cavity 4.

In summary, in a preferred embodiment a threaded connection body 20 is welded to the outer surface of any part of the wall 10 of a pipe, seachest or other flooded cavity 4 within the hull of a ship or floating offshore installation. A sealed cutting apparatus 50 is mounted via a valve unit 30 on the connection body and a cutter extended through the open valve to form an opening 18 in the wall. After retracting the cutter and closing the valve 34, the cutting apparatus is replaced by a sealed inspection unit 70 having a camera which is extended through the valve and the opening 18 to inspect the cavity 4. After retracting the camera and closing the valve 34, the inspection unit is replaced by a plug deployment unit 100 which is used to advance a plug 120 through the open valve and screw it into the connection body 20. The valve unit 30 can then be removed and replaced with a cap 90 so that the plug and the cap provide a double seal to the connection body.

Although in the illustrated embodiment the connection body is installed so that the axis of its bore is normal to length axis of the pipework forming the cavity, it may be adapted to be attached at any desired angle to the wall of the cavity so as to provide an optimal angle of entry for the inspection apparatus in order to advance the camera towards or through the valve gear or other location to be inspected. It is also possible to provide swivelling pressure tight joints and the like through which the insertion angle of the inspection tool may be adjusted.

The connection body may also be used as a port through which to install a temporary plugging device such as an inflatable body as used in the field of maintenance and inspection of underground service pipes and the like to sealingly obstruct the pipe or other cavity. By installing a port and blocking the pipe on both sides of a valve installation, the valve gear can thus be removed and replaced. Optionally, the ports may be used to provide a bypass flowpath through which pressure can be relieved or water can continue to flow past the valve gear undergoing maintenance or replacement.

The novel apparatus may be used as part of a comprehensive inspection regime including the use of ROVs, ultrasonic, eddy current or magnetic particle inspection, and other inspection techniques as known in the art. Of course, rather than using the novel apparatus for visual inspection by means of a camera or the like, any other type of inspection tool may be introduced through the inspection port. The inspection tool may also be flexible or may be mounted on a tether so that it does not require an access path which is axially aligned with the opening in the wall of the cavity. The inspection tool may even be a freely moving body with a wireless control means and without any mechanical connection, with a cooperating inspection body being connected to the valve means and forming a compartment in which the inspection tool is placed before opening the valve to introduce it into the cavity.

Similarly, instead of a holesaw, the penetrator tool could comprise any means as known in the art capable of forming an opening in the wall of the cavity within the pressure retaining compartment. Instead of providing a pilot drill with spring inserts as shown, the retaining means could comprise any capture device, engaging part, or other means for retaining a portion cut from the wall. For example, the penetrator tool may include a magnet. Where a holesaw is used, the cylindrical blade could have retaining elements. Alternatively, the pilot drill could have a collar driven in rotation by a slipping friction clutch and having a hardened thread for biting into the cut washer.

Although in the preferred embodiment the plug is engaged in a female thread so that it fits inside the connection body and the cap engages a male thread so that it fits over the outside of the connection body, the terms "plug" and "cap" should not be construed as limited to respectively internal and external configurations relative to the connection body. Rather, the terms "plug" and "cap" are used to denote elements which sealingly engage the connection body to retain fluid pressure, irrespective of their mechanical configuration. It is conceivable for example for the cap to engage in an internal (female) thread in the connection body, and (less conveniently) for the plug to include a female thread which engages a male threaded part of the connection body through which the cavity communicates with the remainder of the pressure retaining compartment.

In a development, grooves running parallel with the length axis of the cap may be machined in the threads of the cap, or alternatively in the external thread on the connection body, to relieve pressure from the pressure retaining compartment when the seal is broken as the cap (or valve apparatus) is removed. In the unlikely event of failure of the plug, sustained flow of water from the grooves as the cap is unscrewed provides a warning to the operator.

It is strongly preferred to make the connection body from stainless steel or other weldable metal so that it can be attached by welding, which is reliable and space efficient. In less preferred embodiments however it could be attached by clamping or other fixing methods as known in the art, insofar as such methods offer an acceptable guarantee of hull integrity.

Impressed current cathodic protection or other protective systems could be used if preferred instead of a sacrificial anode.

In less preferred embodiments, rather than releasably connecting the penetrator body to the valve body, the penetrator body could be sealingly connected to the connection body (e.g. forming an integral part of the connection body) for once-only operation of the penetrator tool, the captured portion of the wall being retracted and retained together with the penetrator tool in an enlarged pressure retaining compartment. The inspection tool may then be advanced and retracted along an axis which is not collinear with that of the penetrator tool, for example, so that the inspection tool can pass through the opening at an oblique angle relative to the length axis of the pipework defining the cavity. In such embodiments, it would be possible for the penetrator tool to be operated to form the opening before the valve apparatus is attached to the connection body, for example, by arranging a temporary plug in a threaded bore in the connection body to block flow via the second aperture, and afterwards attaching the valve body and plug deployment apparatus and withdrawing the temporary plug via the open valve orifice. It should be understood therefore that the steps of the method may be carried out in any order in accordance with the configuration of the respective parts of the assembly.

The valve apparatus and other parts of the pressure retaining assembly may be connected together and to the connection body either directly or indirectly, e.g. by connecting them to intermediate parts or to other respective parts of the pressure retaining assembly. Similarly, although for pressure integrity and corrosion resistance it is strongly preferred for the connection body to be a unitary part, the connection body and other parts may themselves be assemblies of subcomponents.

In less preferred embodiments, the valve could be left permanently in position, in which case the kit need only include a connection body, valve apparatus, penetrator apparatus and inspection apparatus. The valve could be capped off to form a second (redundant) seal.

The valve apparatus may comprise only the valve (such as a spigot or the like having a transverse bore) which is introduced into a valve orifice (comprising for example a passageway intersecting a cavity for receiving the spigot) forming part of the connection body or other component of the assembly. Similarly, rather than forming part of a subassembly including a body part and a tool part wherein the body part is releasably attached as part of the pressure retaining assembly, either or both of the penetrator tool and the inspection tool could be received in a cooperating aperture or guideway of the connection body or other part of the pressure retaining assembly. The connection body therefore need not be a short cylinder, but may have any desired configuration as long as the first and second apertures are positioned to allow the inspection tool to pass through the opening in the wall of the cavity.

The valve could be any element which is operable to selectively open and close the fluid communication passage defined by the connection body, including for example a threaded stopper or the like, and could be integral with the inspection tool or the penetrator tool. For example, the valve could be a threaded cap or plug arranged on the distal end of the inspection tool or a part of the penetrator tool, and the valve body could be a threaded aperture, the valve being threadedly engaged in the valve body by retracting and then rotating the inspection tool or penetrator tool. It should be understood therefore that in this specification, a valve is construed to mean any element operable to seal a valve orifice.

The inspection body or penetrator body could be sealingly connected to the valve body by forming the inspection body or penetrator body integrally with the valve body, e.g. as a single casting or machined part in bronze or stainless steel. In yet further embodiments, the penetrator tool could be a part of the inspection tool.

Many further adaptations falling within the scope of the claims will be evident to those skilled in the art.

The invention claimed is:

1. A method of inspecting a flooded cavity within a structure, said cavity being defined by a wall having a wet side interior to the cavity and an opposite, dry side exterior to the cavity; the method including:
   providing a plurality of parts including at least a connection body, a valve apparatus, a penetrator apparatus, and an inspection apparatus, and assembling together respective ones of the parts in respective use positions thereof to form a pressure retaining assembly, the pressure retaining assembly including at least the connection body and defining a pressure retaining compartment;

the connection body defining first and second intercommunicating apertures;

the valve apparatus including at least a valve, the valve being operable to selectively open and close a valve orifice;

the penetrator apparatus including at least a penetrator tool;

the inspection apparatus including at least an inspection tool;

and further including sealingly fixing the connection body at the first aperture in its use position to the dry side of the wall of the flooded cavity in a floating condition of said structure wherein said structure is floating and at least partially submerged in a body of water in fluid communication with the cavity so that the wall excludes the water in the cavity from a dry interior space within the structure and the wet side of the wall is exposed to fluid pressure within the cavity, so that the connection body forms in its use position a base portion of the pressure retaining assembly;

and in the use position of the connection body and the penetrator apparatus and the floating condition of the structure, operating the penetrator tool within the pressure retaining compartment to form an opening in the wall of the flooded cavity within the first aperture so as to establish fluid communication between the flooded cavity and the pressure retaining compartment via the opening;

and further including, in the use position of the valve apparatus and the inspection apparatus and the floating condition of the structure, arranging the valve to control fluid communication via the second aperture of the connection body so as to selectively isolate the inspection tool from fluid pressure within the pressure retaining compartment;

and after forming the opening, in the floating condition of the structure, advancing the inspection tool through the open valve orifice, the connection body and the opening into the flooded cavity and inspecting the cavity; and then, in the floating condition of the structure, withdrawing the inspection tool back through the opening, the connection body and the valve orifice and closing the valve.

2. A method according to claim 1, wherein the connection body is welded to the wall in the floating condition of the structure.

3. A method according to claim 1, including after fixing the connection body to the wall and before forming the opening, pressurising the pressure retaining compartment to a test pressure.

4. A method according to claim 1, including providing a protective anode,
deploying the protective anode through the open valve orifice in the floating condition of the structure, and fixing the protective anode so that it is exposed to the water in the flooded cavity.

5. A method according to claim 1, wherein the inspection tool comprises a camera mounted on a shaft, and including, after inserting the shaft via the connection body into the flooded cavity, moving the shaft axially and in rotation about a length axis of the shaft and tilting the camera about an axis transverse to the length axis of the shaft to inspect the cavity.

6. A method according to claim 1, including providing a plug and a plug deployment apparatus;
the plug being releasably sealingly engageable with the connection body;
the plug deployment apparatus including at least a plug deployment tool;
connecting the plug to the plug deployment tool;
and after forming the opening, releasably connecting the plug deployment apparatus in a use position thereof to form part of the pressure retaining assembly;
opening the valve so that the plug is exposed via the open valve orifice to fluid pressure within the pressure retaining compartment;
operating the plug deployment tool to advance the plug through the open valve orifice and releasably sealingly engage the plug with the connection body to form part of the pressure retaining assembly;
detaching the plug deployment tool from the plug; and then
detaching the plug deployment apparatus from the pressure retaining assembly.

7. A method according to claim 6, wherein the valve apparatus is releasably connected in its use position; and including, after releasably sealingly engaging the plug with the connection body, detaching the valve apparatus from the pressure retaining assembly; and, after detaching the valve apparatus from the pressure retaining assembly, releasably sealingly engaging a cap with the connection body in the floating condition of the structure so that the connection body is sealed with both the plug and the cap.

8. A method according to claim 7, including providing the plug with a protective anode, and releasably sealingly engaging the plug with the connection body in the floating condition of the structure so that the anode is exposed to the water in the flooded cavity.

9. An installation in a structure having a flooded cavity in a floating condition of the structure wherein the structure is floating and at least partially submerged in a body of water in fluid communication with the cavity, said cavity being defined by a wall excluding the water in the cavity from a dry interior space within the structure, the wall having a wet side exposed to fluid pressure within the cavity and an opposite, dry side exterior to the cavity;

the installation including a connection body defining first and second intercommunicating apertures, wherein the connection body is sealingly fixed in a use position at the first aperture to the dry side of the wall of the flooded cavity in the floating condition of the structure;

there being further provided a kit of parts including at least a valve apparatus, a penetrator apparatus, and an inspection apparatus;

the valve apparatus including at least a valve, the valve being operable to selectively open and close a valve orifice;

the penetrator apparatus including at least a penetrator tool;

the inspection apparatus including at least an inspection tool;

each of the valve apparatus, penetrator apparatus, and inspection apparatus being connected or connectable in a respective use position to form part of a pressure retaining assembly; the pressure retaining assembly including at least the connection body and defining a pressure retaining compartment in the use position of the connection body, wherein the connection body forms in its use position a base portion of the pressure retaining assembly;

the penetrator tool being operable within the pressure retaining compartment in the use position of the penetrator apparatus to form an opening in the wall of the flooded cavity within the first aperture, so as to establish fluid communication between the flooded cavity and the pressure retaining compartment via the opening in the floating condition of the structure;

the valve being arranged in the use position of the valve apparatus to control fluid communication via the second aperture of the connection body, and to selectively isolate the inspection tool from fluid pressure within the pressure retaining compartment in the use position of the inspection apparatus when the inspection tool is in a retracted position;

the inspection tool being operable in the floating condition of the structure and the use position of the inspection apparatus to extend through the open valve orifice, the connection body and the opening into the flooded cavity so as to inspect the cavity in an extended position, and to retract from the extended position back through the opening, the connection body and the valve orifice from the extended position to the retracted position.

10. A kit of parts for inspecting a flooded cavity within a structure, said structure being at least partially submerged in a body of water in fluid communication with the cavity;

said cavity being defined by a wall excluding the water in the cavity from a dry interior space within the structure, the wall having a wet side exposed to fluid pressure within the cavity and an opposite, dry side exterior to the cavity;

the kit of parts including at least a connection body, a valve apparatus, a penetrator apparatus, and an inspection apparatus;

the connection body defining first and second intercommunicating apertures;

the valve apparatus including at least a valve, the valve being operable to selectively open and close a valve orifice;

the penetrator apparatus including at least a penetrator tool;

the inspection apparatus including at least an inspection tool;

each of the valve apparatus, penetrator apparatus, and inspection apparatus being connected or connectable in a respective use position to form part of a pressure retaining assembly; the pressure retaining assembly including at least the connection body and defining a pressure retaining compartment in a use position of the connection body;

the connection body being sealingly fixable at the first aperture to the dry side of the wall of the flooded cavity to form in its use position a base portion of the pressure retaining assembly;

the penetrator tool being operable within the pressure retaining compartment in the use position of the penetrator apparatus to form an opening in the wall of the flooded cavity within the first aperture, so as to establish fluid communication between the flooded cavity and the pressure retaining compartment via the opening;

the valve being arranged in the use position of the valve apparatus to control fluid communication via the second aperture of the connection body, and to selectively isolate the inspection tool from fluid pressure within the pressure retaining compartment in the use position of the inspection apparatus when the inspection tool is in a retracted position;

the inspection tool being operable in the use position of the inspection apparatus to extend through the open valve orifice, the connection body and the opening into the flooded cavity so as to inspect the cavity in an extended position, and to retract from the extended position back through the opening, the connection body and the valve orifice from the extended position to the retracted position; wherein the connection body is weldable to the wall, and wherein the kit of parts further includes a plug and a plug deployment apparatus;

the plug being releasably sealingly engageable with the connection body;

the plug deployment apparatus including at least a plug deployment tool;

the plug being releasably connectable to the plug deployment tool;

the plug deployment apparatus being releasably connectable in a use position of the plug deployment apparatus to form part of the pressure retaining assembly;

the valve being arranged in the use position of the valve apparatus to selectively isolate the plug deployment tool from fluid pressure within the pressure retaining compartment when the plug deployment apparatus is connected in its use position, the plug is connected to the plug deployment tool, and the plug deployment tool is in a retracted position;

the plug deployment tool being operable in the use position of the plug deployment apparatus to extend from its retracted position through the open valve orifice so as to advance the plug through the open valve orifice and releasably sealingly engage the plug with the connection body to form part of the pressure retaining assembly;

the plug deployment tool further being releasable from the plug when the plug is sealingly engaged with the connection body.

11. A kit of parts according to claim 10, including a pressure testing apparatus, the pressure testing apparatus being arranged to connect the pressure retaining compartment to a pressure source so as to pressurise the pressure retaining compartment to a test pressure in the use position of the connection body and before forming the opening.

12. A kit of parts according to claim 10, including a protective anode, the protective anode being deployable through the open valve orifice to a fixed use position in which it is exposed to the water in the flooded cavity proximate the opening.

13. A kit of parts according to claim 10, including a cap; wherein the valve apparatus is releasable from the pressure retaining assembly,
and the cap is releasably sealingly engageable with the connection body after the plug is releasably sealingly engaged with the connection body and the valve apparatus is released, so as to seal the connection body with both the plug and the cap.

14. A kit of parts according to claim 13, wherein the plug includes a protective anode, and the anode is exposed to the water in the flooded cavity when the plug is releasably sealingly engaged with the connection body.

15. A kit of parts according to claim 10, wherein the inspection tool comprises a camera mounted on a shaft, the shaft being insertable via the connection body into the flooded cavity, and the camera is arranged to tilt about an axis transverse to a length axis of the shaft.

16. A kit of parts according to claim 15, wherein the shaft is moveable axially and in rotation about its length axis when inserted via the connection body into the flooded cavity.

* * * * *